United States Patent [19] [11] 4,254,143
Loewe et al. [45] Mar. 3, 1981

[54] MONOCARBOXYLATES OF PHENYLGUANIDINESULFONIC ACID ESTERS, A PROCESS FOR THEIR MANUFACTURE, COMPOSITIONS CONTAINING THEM AND THEIR USE FOR COMBATING HELMINTHS

[75] Inventors: Heinz Loewe, Kelkheim; Josef Urbanietz, Schwalbach; Dieter Düwel, Hofheim am Taunus; Reinhard Kirsch, Eppstein, all of Fed. Rep. of Germany

[73] Assignee: Hoechst Aktiengesellschaft, Frankfurt am Main, Fed. Rep. of Germany

[21] Appl. No.: 68,532

[22] Filed: Aug. 16, 1979

[30] Foreign Application Priority Data

Aug. 19, 1978 [DE] Fed. Rep. of Germany ....... 2836385

[51] Int. Cl.$^3$ ..................... A61K 31/27; C07C 143/68

[52] U.S. Cl. ................................ 424/300; 260/397.6; 260/456 A

[58] Field of Search ........................ 260/456 A, 397.6; 424/300, 228

[56] References Cited

U.S. PATENT DOCUMENTS

| 3,996,368 | 12/1976 | Loewe et al. ..................... 260/456 A |
| 3,996,369 | 12/1976 | Loewe et al. ..................... 260/456 A |
| 4,024,176 | 5/1977 | Kölling et al. ..................... 260/397.6 |
| 4,088,780 | 5/1978 | Kölling et al. .......................... 560/13 |
| 4,127,670 | 11/1978 | Wollweber et al. ................... 560/13 |

*Primary Examiner*—Nicky Chan
*Attorney, Agent, or Firm*—Curtis, Morris & Safford

[57] ABSTRACT

New monocarboxylates of phenylguanidinesulfonic acid esters and a process for their manufacture are described. They are effective as medicaments against helminths and liver flukes when administered orally or parenterally.

4 Claims, No Drawings

MONOCARBOXYLATES OF PHENYLGUANIDINESULFONIC ACID ESTERS, A PROCESS FOR THEIR MANUFACTURE, COMPOSITIONS CONTAINING THEM AND THEIR USE FOR COMBATING HELMINTHS

It is known that phenylguanidines of the formula

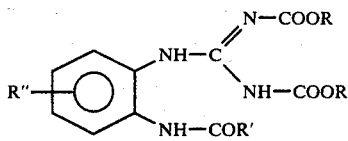

in which R denotes lower alkyl, R' denotes lower alkyl or hydrogen and R" denotes —$C_4H_9$, —$COC_6H_5$, —$OC_6H_5$ or —$SC_6H_5$, have an anthelmintic activity (compare German Offenlegungsschriften Nos. 2,117,293, 2,250,911, 2,304,764 and 2,423,679).

These phenylguanidines, and also anthelmintics belonging to the class of the 2-benzimidazoles carbamates, such as parbendazole, mebendazole, fenbendazole and other representatives of this class of compounds, are only slightly soluble in water and therefore can only be administered orally to humans and animals. These substances do not readily allow the preparation of solutions which can be administered parenterally and are well tolerated topically, such as are particularly required in the treatment of large animals, such as cattle, horses and pigs.

Furthermore, methoxycarbonylphenylguanidines of the formula

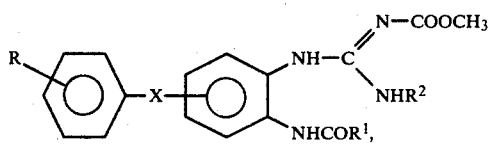

in which X represents oxygen, sulfur or the —SO—, —$SO_2$— or —CO— group and in which X is linked to the phenylguanidino radical in position 4 or 5, R denotes hydrogen, halogen, $C_1$–$C_4$ alkoxy or trifluoromethyl, $R^1$ denotes hydrogen, optionally substituted alkyl, optionally substituted alkoxy, optionally substituted alkoxyalkyl or optionally substituted aralkyl, and $R^2$ denotes hydrogen, alkyl, cycloalkyl, cycloalkylalkyl or aralkyl, the salts of which with inorganic or organic acids are soluble in water and can therefore be administered parenterally, are known from German Offenlegungsschrift No. 2,630,847. Although they are effective against a broad spectrum of nematodes, they are not adequately effective against liver fluke, a parasite which often is present together with the nematodes of the gastro-intestinal tract and is preferably combated together with the nematodes.

Benzimidazole carbamates of the formula

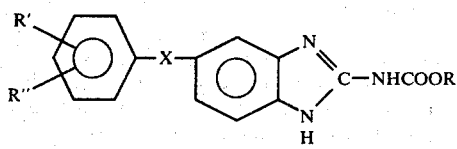

in which X denotes the group —$OSO_2$— or —$SO_2O$—, R denotes alkyl having 1 to 4 C atoms and R' and R" denote, in each case independently of one another, hydrogen, hydroxyl, alkyl or alkoxy having 1–4 C atoms in each case, halogen, trifluoromethyl or CN, which are effective against both nematodes and liver flukes, are admittedly known from German Offenlegungsschriften Nos. 2,441,201 and 2,441,202, but they can only be administered orally because of their low solubility in water.

The invention relates to monocarboxylates of phenylguanidinesulfonic acid esters of the formula I

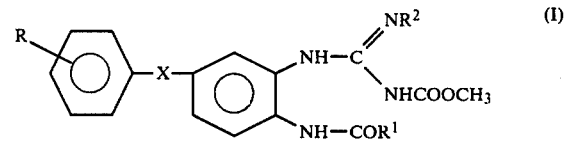

in which X denotes —$OSO_2$— or —$SO_2O$—, R denotes hydrogen, halogen, alkyl having 1–4 C atoms, alkoxy having 1–4 C atoms, —CN or —$CF_3$, $R^1$ denotes hydrogen, optionally substituted alkyl, optionally substituted alkoxy, optionally substituted alkoxyalkyl or optionally substituted aralkyl and $R^2$ denotes hydrogen, alkyl, cycloalkyl, cycloalkylalkyl or aralkyl, and to their physiologically acceptable salts with organic or inorganic acids.

The compounds, according to the invention, of the formula I are basic in character. They can be used as anthelmintic active compounds, in the from of free bases or in the form of their salts with physiologically acceptable inorganic and organic acids, for example hydrogen halides, preferably hydrochlorides, sulfates, phosphates, nitrates, maleates, fumarates, acetates, propionates, lactates, methanesulfonates or naphthalenedisulfonates.

The invention also relates to a process for the manufacture of the monocarboxylates of phenylguanidinesulfonic acid esters of the formula I, which comprises (a) reacting a substituted aniline derivative of the formula II

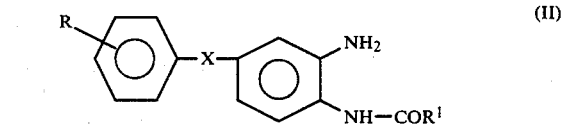

in which X, R and $R^1$ have the meanings indicated for formula I, either ($a_1$) with an isothiourea derivative of the formula III

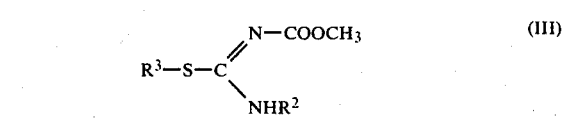

in which $R^2$ has the meaning indicated for formula I and $R^3$ represents alkyl having 1–4 C atoms, or ($a_2$) with an O-methylisourea derivative of the formula IIIa

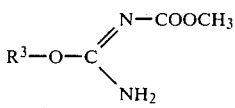

(IIIa)

in which R³ represents alkyl having 1–4 C atoms, in the presence of a solvent and optionally in the presence of an acid, or (b) hydrolyzing a phenylguanidine-bis-carboxylate of the formula IV

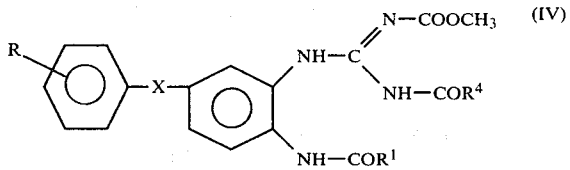

in which X, R and R¹ have the meanings indicated above and R⁴ represents alkyl or alkoxy, and, if appropriate, alkylating a compound of the formula I, thus obtained, in which R² denotes hydrogen.

In the formula I to IV, the substituents have the following preferred meanings: As a halogen, R represents fluorine, chlorine and bromine, particularly fluorine and chlorine. $C_1$–$C_4$ alkoxy represents methoxy, ethoxy, n-propoxy, i-propoxy, n-butoxy, i-butoxy and t-butoxy, preferably methoxy and ethoxy. As optionally substituted alkyl, R¹ represents straight-chain or branched alkyl which preferably contains 1 to 6, in particular 1 to 4, carbon atoms. Optionally substituted methyl, ethyl, n-propyl, i-propyl, n-butyl, i-butyl and t-butyl may be mentioned as examples. As optionally substituted alkoxy, R¹ represents straight-chain or branched alkoxy which preferably contains 1 to 6, in particular 1 to 4, carbon atoms. Optionally substituted methoxy, ethoxy, n-propoxy, i-propoxy, n-butoxy, i-butoxy and t-butoxy may be mentioned as examples. As optionally substituted alkoxyalkyl, R¹ represents straight-chain or branched alkoxyalkyl which preferably contains 1 to 6, particularly 1 to 4, carbon atoms in the alkoxy part and preferably contains 1 to 6, particularly 1 to 4, carbon atoms in the alkyl part. Optionally substituted methoxymethyl, methoxyethyl, ethoxymethyl and ethoxyethyl may be mentioned as examples. As optionally substituted aralkyl, R¹ represents aralkyl which is optionally substituted in the aryl part and/or the alkyl part and preferably contains 6 to 10 carbon aoms in the aryl part and preferably contains 1 to 4, particularly 1 or 2, carbon atoms in the alkyl part, it being possible for the alkyl part to be straight-chain or branched. Optionally substituted benzyl and phenylethyl may be mentioned as examples.

The various radicals R¹ can carry one or more, preferably 1 to 3 and more particularly 1 or 2, identical or different substituents. The following may be cited as examples of substituents: alkoxy which preferably contains 1 to 4, particularly 1 or 2, carbon atoms, such as methoxy, ethoxy, n-propoxy, i-propoxy, n-butoxy, i-butoxy and t-butoxy; alkylthio which preferably contains 1 to 4, particularly 1 or 2, carbon atoms, such as methylthio, ethylthio, n-propylthio, i-propylthio, n-butylthio, i-butylthio and t-butylthio; halogenoalkyl which preferably contains 1 to 4, particularly 1 or 2, carbon atoms and preferably contains 1 to 5, particularly 1 to 3, halogen atoms, the halogen atoms being identical or different and preferably being fluorine, chlorine or bromine, particularly fluorine, such as trifluoromethyl; hydroxyl; halogen, preferably fluorine, chlorine, bromine and iodine and particularly fluorine and chlorine; cyano; nitro; amino; monoalkylamino and dialkylamino which preferably contain 1 to 4, particularly 1 or 2, carbon atoms per alkyl group, such as methylamino, methylethylamino, n-propylamino, i-propylamino and methyl-n-butylamino; carboalkoxy which preferably contains 2 to 4, particularly 2 or 3, carbon atoms, such as carbomethoxy and carboethoxy; sulfo (—$SO_3H$); alkylsulfonyl which preferably contains 1 to 4, particularly 1 or 2, carbon atoms, such as methylsulfonyl and ethylsulfonyl; and arylsulfonyl which preferably contains 6 or 10 aryl carbon atoms, such as phenylsulfonyl. As alkyl, R² represents straight-chain or branched alkyl preferably containing 1 to 6, particularly 1 to 4 carbon atoms. Methyl, ethyl, n-propyl, i-propyl, n-butyl, i-butyl and t-butyl may be mentioned as examples. As cycloalkyl, R² represents monocyclic, bicyclic and tricyclic cycloalkyl which preferably contain 3 to 10, particularly 3, 5 or 6, carbon atoms. Cyclopropyl, cyclobutyl, cyclopentyl, cyclohexyl, cycloheptyl, bicyclo-[2.2.1.]-heptyl, bicyclo-[2.2.2]-octyl and adamantyl may be mentioned as examples. As cycloalkylalkyl, R² represents cycloalkylalkyl which preferably contains 3 to 10, particularly 3, 5 or 6, carbon atoms in the cycloalkyl part and preferably contains 1 to B 6, particularly 1 to 4, carbon atoms in the alkyl part. Cyclopropylmethyl, cyclopentylmethyl, cyclohexylmethyl, cyclopropylethyl, cyclopentylethyl and cyclohexylethyl may be mentioned as examples. As aralkyl, R² represents aralkyl which preferably contains 6 or 10, particularly 6, carbon atoms in the aryl part and preferably contains 1 to 4, particularly 1 or 2, carbon atoms in the alkyl part, it being possible for the alkyl part to be straight-chain or branched. Benzyl and phenylethyl may be mentioned as examples. R³ as $C_1$–$C_2$ alkyl in the formula III represents methyl, ethyl, n-propyl, i-propyl, n-butyl, i-butyl and t-butyl, particularly methyl and ethyl. R⁴ as alkyl represents straight-chain or branched alkyl which preferably contains 1 to 6, particularly 1 to 4, carbon atoms. Methyl, ethyl, n-propyl, i-propyl, n-butyl, i-butyl and t-butyl may be mentioned as examples. R⁴ as alkoxy represents straight-chain or branched alkoxy which preferably contains 1 to 6, particularly 1 to 4, carbon atoms. Methoxy, ethoxy, n-propoxy, i-propoxy, n-butoxy, i-butoxy and t-butoxy may be mentioned as examples.

Amongst the monocarboxylates of phenylguanidine-sulfonic acid esters of the formula I, those in which the substituent R denotes hydrogen, chlorine, trifluoromethyl or —CN, the substituent R¹ denotes hydrogen, methyl, ethyl, propyl, isopropyl or methoxymethyl and the substituent R² denotes hydrogen, have proved particularly suitable as anthelmintics.

The substituted aniline derivatives of the formula II which are used as starting materials and the phenylguanidine derivatives of the formula IV, as well as processes for their manufacture, are known from German Offenlegungsschrift No. 2,608,238. Some of the isothioureas of the formula III are known. They can be obtained by reacting optionally substituted S-alkylisothioureas with chloroformic acid methyl ester. The following isothioureas of the formula III may be mentioned individually as examples: N-methoxycarbonyl-S-methylisothiourea, N-methoxycarbonyl-N'-methyl-S- methylisothiourea, N-methoxycarbonyl-N'-ethyl-S-methylisothiourea, N-methoxycarbonyl-N'-propyl-S-methylisothiourea, N-methoxycarbonyl-N'-isopropyl-S-methylisothiourea, N-methoxycarbonyl-N'-butyl-S-methylisothiourea, N-methoxycarbonyl-N'-isobutyl-S-methylisothiourea, N-methoxycarbonyl-N'-tert.-butyl-S-methylisothiourea, N-methoxycarbonyl-N'-cyclohexyl-S-methylisothiourea, N-methoxycarbonyl-N'-cyclohexylmethyl-S-methylisothiourea, N-methoxycarbonyl-N'-benzyl-S-methylisothiourea, N-methoxycarbonyl-N'-α-phenethyl-S-methylisothiourea and N-methoxycarbonyl-N'-β-phenethyl-S-methylisothiourea.

The O-methylisoureas of the formula IIIa can be obtained by reacting corresponding O-alkylisoureas with chloroformic acid methyl ester.

Suitable solvents for the reaction of compounds of the formula II with substances of the formula III or IIIa are all polar organic solvents, preferably alcohols, such as methanol and isopropanol, and mixtures thereof with water, ketones, such as acetone, and mixtures thereof with water, and also ethers, such as dioxane or tetrahydrofuran.

Any desired organic or inorganic acids can be used as catalysts in the preparation of the compounds of the formula I from compounds of the formula II and substances of the formula III or IIIa. It is advantageous to use readily accessible acids, such as hydrochloric acid, sulfuric acid, nitric acid, formic acid, acetic acid or p-toluene-sulfonic acid. The reaction temperatures employed in the preparation can vary within a range. In general, the reaction is carried out at between 0° C. and 120° C., preferably between 10° and 30° C. In general the reaction is carried out under normal pressure. The reaction of compounds of the formula II with compounds of the formula III or IIIa is preferably carried out using equimolar quantities.

The hydrolysis of the compounds of the formula IV is preferably carried out by heating in an alcohol, such as methanol, ethanol or isopropanol, or mixtures thereof with water, in the presence of a base, for example an aliphatic amine, such as methylamine, butylamine, piperidine or N-methylpiperazine, in the presence of an alcoholate, such as sodium methylate, or in the presence of an inorganic base, such as KOH or NaOH. Solutions of butylamine in methanol or ethanol have proved particularly suitable. The hydrolysis can also be carried out by prolonged heating with water in the presence of a solvent, such as acetone. The reaction temperatures of the hydrolysis reaction can be varied within a fairly wide range; in general the reaction is carried out at between 0° C. and 120° C., preferably between 40° C. and 100° C. In general the reaction is carried out under normal pressure. In basic media, the reaction is in general complete after only a few minutes.

The monocarboxylates of phenylguanidinesulfonic acid esters of the formula I comprise, for example, the following compounds: N-(2-acetamido-5-phenylsulfonyloxyphenyl)-N'-methoxycarbonylguanidine, N-(2-formamido-5-phenylsulfonyloxyphenyl)-N'-methoxycarbonylguanidine, N-(2-propionamido-5-phenylsulfonyloxyphenyl)-N'-methoxycarbonylguanidine, N-(2-butyramido-5-phenylsulfonyloxyphenyl)-N'-methoxycarbonylguanidine, N-(2-isobutyramido-5-phenylsulfonyloxyphenyl)-N'-methoxycarbonylguanidine, N-(2-valeramido-5-phenylsulfonyloxyphenyl)-N'-methoxycarbonylguanidine, N-(2-isocaleramido-5-phenylsulfonyloxyphenyl)-N'-methoxycarbonylguanidine, N-(2-caproamido-5-phenylsulfonyloxyphenyl)-N'-methoxycarbonylguanidine, N-(2-isocaproamido-5-phenylsulfonyloxyphenyl)-N'-methoxycarbonylguanidine, N-(2-methoxyacetamido-5-phenylsulfonyloxyphenyl)-N'-methoxycarbonylguanidine, N-(2-acetamido-5-(4-chlorophenylsulfonyloxy)-phenyl)-N'-methoxycarbonylguanidine, N-(2-acetamido-5-(3-chlorophenylsulfonyloxy)-phenyl)-N'-methoxycarbonylguanidine, N-(2-acetamido-5-(2-chlorophenylsulfonyloxy)-phenyl)-N'-methoxycarbonylguanidine, N-(2-methoxyacetamido-5-(3-chlorophenylsulfonyloxy)-phenyl)-N'-methoxycarbonylguanidine, N-(2-methoxyacetamido-5-(3-bromophenylsulfonyloxy)-phenyl)-N'-methoxycarbonylguanidine, N-(2-methoxyacetamido-5-(3-methylphenylsulfonyloxy)-phenyl)-N'-methoxycarbonylguanidine, N-(2-methoxyacetamido-5-(3-tert.-butylphenylsulfonyloxy)-phenyl)-N'-methoxycarbonylguanidine, N-(2-methoxyacetamido-5-(3-methoxyphenylsulfonyloxy)-phenyl)-N'-methoxycarbonylguanidine, n-(2-methoxyacetamido-5-(3-ethoxyphenylsulfonyloxy)-phenyl)-N'-methoxycarbonylguanidine, N-(2-methoxyacetamido-5-(3-propoxyphenylsulfonyloxy)-phenyl)-N'-methoxycarbonylguanidine, N-(2-methoxyacetamido-5-(3-isopropoxyphenylsulfonyloxy)-phenyl)-N'-methoxycarbonylguanidine, N-(2-methoxyacetamido-5-(3-butoxyphenylsulfonyloxy)-phenyl)-N'-methoxycarbonylguanidine, N-(2-methoxyacetamido-5-(3-isobutoxyphenylsulfonyloxy)-phenyl)-N'-methoxycarbonylguanidine, N-(2-methoxyacetamido-5-(4-cyanophenylsulfonyloxy)-phenyl)-N'-methoxycarbonylguanidine, N-(2-methoxyacetamido-5-(3-trifluoromethylphenylsulfonyloxy)-phenyl)-N'-methoxycarbonylguanidine, N-(2-methoxyacetamido-5-(3-chloro-4-methylphenylsulfonyloxy)-phenyl)-N'-methoxycarbonylguanidine, N-(2-propionamido-5-(3-trifluoromethylphenylsulfonyloxy)-phenyl)-N'-methoxycarbonylguanidine, N-(2-butyramido-5-(3-trifluoromethylphenylsulfonyloxy)-phenyl)-N'-methoxycarbonylguanidine, N-(2-formamido-5-(3-trifluoromethylphenylsulfonyloxy)-phenyl)-N'-methoxycarbonylguanidine, N-(2-methoxyacetamido-5-phenylsulfonyloxyphenyl)-N'-methoxycarbonyl-N''-methylguanidine, N-(2-methoxyacetamido-5-phenylsulfonyloxyphenyl)-N'-methoxycarbonyl-N''-butylguanidine, N-(2-methoxyacetamido-5-phenylsulfonyloxyphenyl)-N'-methoxycarbonyl-N''-cyclohexylguanidine, N-(2-formamido-5-phenylsulfonyloxyphenyl)-N'-methoxycarbonyl-N'' -methylguanidine, N-(2-propionamido-5-phenylsulfonyloxyphenyl)-N'-methoxycarbonyl-N''-methylguanidine, N-(2-butyramido-5-phenylsulfonyloxyphenyl)-N'-methoxycarbonyl-N''-methylguanidine, N-(2-acetamido-5-phenoxysulfonylphenyl)-N'-methoxycarbonylguanidine, N-(2-butyramido-5-phenoxysulfonylphenyl)-N'-methoxycarbonylguanidine, N-(2-isobutyramido-5-phenoxysulfonylphenyl)-N'-methoxycarbonylguanidine, N-(2-valeramido-5-phenoxysulfonylphenyl)-N'-methoxycarbonylguanidine, N-(2-isovaleramido-5-phenoxysulfonylphenyl)-N'-methoxycarbonylguanidine, N-(2-caproamido-5-phenoxysulfonylphenyl)-N'-methoxycarbonylguanidine, N-(2-isocaproamido-5-phenoxysulfonylphenyl)-N'-methoxycarbonylguanidine, N-(2-methoxyacetamido-5-phenoxysulfonylphenyl)-N'-methoxycarbonylguanidine, N-(2-acetamido-5-(4-chlorophenoxysulfonyl)-phenyl)-N'-methoxycarbonylguanidine, N-(2-acetamido-5-(3-chlorophenoxysulfonyl)-phenyl)-N'-methoxycarbonylguanidine, N-(2-acetamido-5-(2-chlorophenoxysulfonyl)-phenyl)-N'-methoxycarbonylguanidine, N-(2-methoxyacetamido-5-

(3-chlorophenoxysulfonyl)-phenyl)-N'-methoxycarbonylguanidine, N-(2-methoxyacetamido-5-(3-bromophenoxysulfonyl)-phenyl)-N'-methoxycarbonylguanidine, N-(2-methoxyacetamido-5-(3-methylphenoxysulfonyl)-phenyl)-N'-methoxycarbonylguanidine, N-(2-methoxyacetamido-5-(3-tert.-butylphenoxysulfonyl)-phenyl)-N'-methoxycarbonylguanidine, N-(2-methoxyacetamido-5-(3-methoxyphenoxysulfonyl)-phenyl)-N'-methoxycarbonylguanidine, N-(B 2-methoxyacetamido-5-(3-ethoxyphenoxysulfonyl)-phenyl)-N'-methoxycarbonylguanidine, N-(2-methoxyacetamido-5-(3-propoxyphenoxysulfonyl)-phenyl)-N'-methoxycarbonylguanidine, N-(2-methoxyacetamido-5-(3-isopropoxyphenoxysulfonyl)-phenyl)-N'-methoxycarbonylguanidine, N-( 2-methoxyacetamido-5-(3-butoxyphenoxysulfonyl)-phenyl)-N'-methoxycarbonylguanidine, N-(2-methoxyacetamido-5-(3-isobutoxyphenoxysulfonyl)-phenyl)-N'-methoxycarbonylguanidine, N-(2-methoxyacetamido-5-(4-cyanophenoxysulfonyl)-phenyl)-N'-methoxycarbonylguanidine, N-(2-methoxyacetamido-5-(3-trifluoromethylphenoxysulfonyl)-phenyl)-N'-methoxycarbonylguanidine, N-(2-methoxyacetamido-5-(3-chloro-4-methylphenoxysulfonyl)-phenyl)-N'-methoxycarbonylguanidine, N-(2-propionamido-5-(3-trifluoromethylphenoxysulfonyl)-phenyl)-N'-methoxycarbonylguanidine, N-(2-butyramido-5-(3-trifluoromethylphenoxysulfonyl)-phenyl)-N'-methoxycarbonylguanidine, N-(2-formamido-5-(3-trifluoromethylphenoxysulfonyl)-phenyl)-N'-methoxycarbonylguanidine, N-(2-methoxyacetamido-5-phenoxysulfonylphenyl)-N'-methoxycarbonyl-N''-methylguanidine, N-(2-methoxyacetamido-5-phenoxysulfonylphenyl)-N'-methoxycarbonyl-N''-butylguanidine, N-(2-methoxyacetamido-5-phenoxysulfonylphenyl)-N'-methoxycarbonyl-N''-cyclohexylguanidine, N-(2-formamido-5-phenxoysulfonylphenyl)-N'-methoxycarbonyl-N''-methylguanidine, N-(2-propionamido-5-phenoxysulfonylphenyl)-N'-methoxycarbonyl-N''-methylguanidine and N-(2-butyramido-5-phenoxysulfonylphenyl)-N'-methoxycarbonyl-N''-methylguanidine.

The monocarboxylates of the phenylguanidinesulfonic acid esters of the formula I according to the invention are valuable chemotherapeutic agents and are suitable for combating parasitic diseases in humans and animals, in particular for combating helminths and liver flukes. They are particularly effective against a large number of helminths, for example Haemonchus, Trichlostrongylus, Ostertagia, Stronglyoides, Cooperia, Chabertia, Oesophagostomum, Hyostrongulus, Ankylostoma, Ascaris and Heterakis and Fasciola. They have a particular marked activity against gastro-intestinal strongylids and liver flukes, with which ruminants, above all, are infected. The compounds according to the invention can therefore be used, in particular, in veterinary medicaments.

In contrast to the compounds known from German Offenlegungsschriften Nos. 2,117,293, 2,250,911, 2,304,764 and 2,423,679, the compounds, according to the invention, of the formula I can advantageously be administered parenterally and, in contrast to the compounds known from German Offenlegungsschrift No. 2,630,847, they are active, surprisingly, against both nematodes and liver flukes.

Depending on the condition of the case, the compounds of the formula I are administered for a period of 1 to 14 days in dosages between 0.5 and 50 mg per kg of body weight.

Compositions as tablets, dragees, capsules, powders, granules or pastes which contain the active compounds together with customary auxiliary substances or excipients, such as starch, cellulose powder, talc, magnesium stearate, sugar, gelatin, calcium carbonate, finely dispersed silica, carboxymethylcellulose or similar substances, are suitable for oral administration.

The products of the process not only have an excellent action when administered orally, but are also active when administered parenterally.

For parenteral administration, a compound of the formula I is either dissolved in one equivalent of an inorganic or organic acid or a salt of these compounds is dissolved in water.

The fact that it is possible to administer the compounds of the formula I parenterally constitutes a considerable advance in the anthelmintic treatment of animals, such as cattle, horses, pigs, sheep, dogs, cats and the like. This form of administration is particularly suitable for the mass treatment of large animals, such as cattle and horses, especially if these animals are at the same time infected with liver flukes.

Preparation examples (Process a₁)

EXAMPLE 1.1

A mixture of 3.4 g of 2-methoxyacetamido-5-phenylsulfonyloxyaniline (formula II), 25 ml of methanol, 3 ml of glacial acetic acid and 2 g of N-methoxycarbonyl-S-methylisothiourea (formula III) is heated under reflux for one day. After standing overnight at room temperature, the N-(2-methoxyacetamido-5-phenylsulfonyloxyphenyl)-N'-methoxycarbonylguanidine (formula I) which has precipitated is filtered off. Yield 0.4 g; melting point 190° C.

The following are obtained by an analogous procedure from substituted 2-acylamidoaniline derivatives (formula II) and N-substituted N-methoxycarbonyl-S-methylisothioureas (formula III):

1.2 N-(2-Formamido-5-phenylsulfonyloxyphenyl)-N'-methyl-N''-methoxycarbonylguanidine 1.3 N-(2-Acetamido-5-phenylsulfonyloxyphenyl)-N'-methyl-N''-methoxycarbonylguanidine 1.4 N-(2-Methoxyacetamido-5-phenylsulfonyloxyphenyl)-N'-methyl-N''-methoxycarbonylguanidine 1.5 N-(2-Propionamido-5-phenylsulfonyloxyphenyl)-N'-methyl-N''-methoxycarbonylguanidine 1.6 N-(2-Methoxyacetamido-5-phenylsulfonyloxyphenyl)-N'-ethyl-N''-methoxycarbonylguanidine 1.7 N-(2-Methoxyacetamido-5-phenylsulfonyloxyphenyl)-N'-propyl-N''-methoxycarbonylguanidine 1.8 N-(2-Methoxyacetamido-5-phenylsulfonyloxyphenyl)-N'-butyl-N''-methoxycarbonylguanidine 1.9 N-(2-Methoxyacetamido-5-phenylsulfonyloxyphenyl)-N'-isobutyl-N''-methoxycarbonylguanidine 1.10 N-(2-Methoxyacetamido-5-phenylsulfonyloxyphenyl)-N'-cyclohexyl-N''-methoxycarbonylguanidine 1.11 N-(2-Methoxyacetamido-5-phenylsulfonyloxyphenyl)-N'-cyclohexylmethyl-N''-methoxycarbonylguanidine 1.12 (2-Methoxyacetamido-5-phenylsulfonyloxyphenyl)-N'-benzyl-N''-methoxycarbonylguanidine.

(Process a₂)

EXAMPLE 2

A mixture of 3.4 g of 2-methoxyacetamido-5-phenylsulfonyloxyaniline (formula II), 25 ml of methanol, 3 ml of glacial acetic acid and 2 g of N-methoxycarbonyl-O-methylisourea (formula IIIa) is heated under reflux for one day. After standing overnight at room temperature, the liquid is filtered from impurities which have precipitated, the filtrate is evaporated to dryness, the residue is taken up in ethyl acetate and washed several times with water and the solvent is evaporated under reduced pressure, after drying with MgSO₄. The N-(2-methoxyacetamido-5-phenyloxyphenyl)-N'-methoxycarbonylguanidine (formula I) which has been formed is obtained in a pure form by stirring the residue with 0.5 N HCl at room temperature and precipitating the product from the filtrate with ammonia. According to thin layer chromatography, it is identical with the process product obtained in accordance with Example 1.

Preparation of the starting material of the formula IIIa: 246 g of O-methylisourea sulfate are dissolved in 300 ml of water and 163 ml of chloroformic acid methyl ester are added dropwise at 10° C., followed by 170 g of NaOH, dissolved in 510 ml of water. The mixture is stirred at room temperature for a further 3 hours. The reaction solution is then extracted with ethyl acetate and this extract is dried with anhydrous sodium sulfate. Evaporation under reduced pressure at a maximum bath temperature of 40° C. gives the N-methoxycarbonyl-O-methylisourea as an oil, which gradually solidifies to form crystals with a melting point of 40° C. Yield 150 g.

(Process b) (hydrolysis)

EXAMPLE 3

A mixture of 2 g of N-(2-methoxyacetamido-5-phenylsulfonyloxyphenyl)-N',N''-bismethoxycarbonylguanidine (formula IV), 20 ml of methanol and 2 ml of butylamine is stirred for 10 minutes at 50° C. A clear solution has already been formed after 2 minutes and shortly afterwards the N-(2-methoxyacetamido-5-phenylsulfonyloxyphenyl)-N'-methoxycarbonylguanidine (formula I) precipitates from this solution. The reaction mixture is allowed to stand for some hours at 10° C. and the precipitate is filtered off and washed with methanol. Yield 1.7 g; melting point 190° C. (decomposition). The process product is identical with that obtained in accordance with Example 1.

The N-(2-methoxyacetamido-5-phenylsulfonyloxyphenyl)-N',N''-bismethoxycarbonylguanidine (formula IV) required for carrying out the reaction is obtained in accordance with German Offenlegungsschrift No. 2,608,238, Example 5.2

A 40% strength aqueous solution of methylamine, piperidine or N-methylpiperazine can also be employed instead of butylamine, using the same procedure. Corresponding results are also obtained with sodium hydroxide solution, ammonia or sodium methylate in alcoholic solution.

EXAMPLE 4 (STILL PROCESS B))

The compounds of the formula I listed in the table which follows are prepared, analogously to Example 3, from the corresponding starting materials of the formula IV in which X denotes —SO₂—O— and R⁴ denotes —OCH₃, respectively:

| | Starting material of the formula IV | | |
|---|---|---|---|
| R¹ | R | Example No. of German Offenlegungsschrift 2,608,238 from which known | Melting point [°C.] of the process product of the formula 1 |
| 2.1 CH₃ | H | 4.1 | 175 |
| 2.2 C₂H₅ | H | 5.3 | 149 |
| 2.3 C₃H₇ | H | 5.1 | 148 |
| 2.4 iC₃H₇ | H | 5.4 | |
| 2.5 C₄H₉ | H | 5.5 | |
| 2.6 iC₄H₉ | H | 5.6 | |
| 2.7 C₅H₁₁ | H | 5.7 | |
| 2.8 iC₅H₁₁ | H | 5.8 | |
| 2.9 cycloC₅H₉ | H | 5.9 | |
| 2.10 cycloC₆H₁₁ | H | 5.10 | |
| 2.11 CH₂C₆H₅ | H | 5.11 | |
| 2.12 CH₂OC₆H₅ | H | 5.12 | |
| 2.13 CH₃ | 4-Cl | 6.1 | |
| 2.14 CH₃ | 3-Cl | 6.2 | |
| 2.15 C₃H₇ | 3-Cl | 6.10 | |
| 2.16 CH₂OCH₃ | 3-Cl | 6.11 | |
| 2.17 C₃H₇ | 2-Cl | 6.12 | |
| 2.18 CH₃ | 2,5-Cl | 6.13 | |
| 2.19 C₃H₇ | 3,5-Cl | 6.14 | |
| 2.10 CH₃ | 4-Br | 6.15 | |
| 2.21 C₂H₅ | 3-Br | 6.16 | |
| 2.22 C₃H₇ | 3-Br | 6.17 | |
| 2.23 CH₂OCH₃ | 3-Br | 6.18 | |
| 2.24 CH₃ | 2-Br | 6.19 | |
| 2.25 CH₃ | 4-CH₃ | 6.20 | |
| 2.26 CH₃ | 3-CH₃ | 6.21 | |
| 2.27 C₂H₅ | 3-CH₃ | 6.22 | |
| 2.28 C₃H₇ | 3-CH₃ | 6.23 | |
| 2.29 CH₂OCH₃ | 3-CH₃ | 6.24 | |
| 2.30 CH₃ | 2-CH₃ | 6.25 | |
| 2.31 CH₃ | 4-t.Butyl | 6.26 | |
| 2.32 CH₃ | 2,4-CH₃ | 6.27 | |
| 2.33 CH₃ | 2-Cl-4-CH₃ | 6.28 | |
| 2.34 CH₃ | 3,4-Cl | 6.29 | |
| 2.35 CH₃ | 3-CF₃ | 6.30 | 182 |
| 2.36 CH₂OCH₃ | 3-CF₃ | 6.31 | 189 |
| 2.37 C₂H₅ | 3-CF₃ | 6.32 | 154 |
| 2.38 C₃H₇ | 3-CF₃ | 6.33 | 168 |
| 2.39 CH₃ | 4-OCH₃ | 6.38 | |
| 2.40 CH₃ | 3-OCH₃ | 6.39 | |
| 2.41 CH₃ | 3-OC₂H₅ | 6.40 | |
| 2.42 CH₃ | 3-CN | 6.41 | |
| 2.43 C₂H₅ | 3-CN | 6.42 | |
| 2.44 C₃H₇ | 3-CN | 6.43 | |
| 2.45 CH₂OCH₃ | 3-CN | 6.44 | |
| 2.46 C₆H₁₁ | 3-CF₃ | 6.45 | |
| 2.47 CH₂OCH₃ | 3-OCH₃ | 6.46 | |
| 2.48 C₂H₅ | 3-OCH₃ | 6.47 | |
| 2.49 H | H | | |

EXAMPLE 5 (STILL PROCESS B))

The compounds of the formula I listed in the table which follows are prepared, analogously to Example 3, from the corresponding starting materials of the formula IV in which X denotes —O—SO₂— and R⁴ denotes —OCH₃ respectively:

| | Starting material of the formula IV | | |
|---|---|---|---|
| R¹ | R | Example No. of German Offenlegungsschrift 2,608,238 from which known | Melting point [°C.] of the process product of the formula 1 |
| 3.1 CH₃ | H | 1.1 | 196 |
| 3.2 CH₂OCH₃ | H | 2.2 | 203 |
| 3.3 C₂H₅ | H | 2.3 | 168 |

-continued

| R¹ | R | Example No. of German Offenlegungsschrift 2,608,238 from which known | Melting point [°C.] of the process product of the formula 1 |
|---|---|---|---|
| 3.4 C₃H₇ | H | 2.1 | 194 |
| 3.5 iC₃H₇ | H | 2.4 | |
| 3.6 C₄H₉ | H | 2.5 | |
| 3.7 iC₄H₉ | H | 2.6 | |
| 3.8 C₅H₁₁ | H | 2.7 | |
| 3.9 iC₅H₁₁ | H | 2.8 | |
| 3.10 cycloC₅H₉ | H | 2.9 | |
| 3.11 cycloC₆H₁₁ | H | 2.10 | |
| 3.12 CH₂C₆H₅ | H | 2.11 | |
| 3.13 CH₂OC₆H₅ | H | 2.12 | |
| 3.14 CH₃ | 4-Cl | 3.1 | |
| 3.15 CH₃ | 3-Cl | 3.2 | |
| 3.16 C₃H₇ | 3-Cl | 3.10 | |
| 3.17 CH₂OCH₃ | 3-Cl | 3.11 | |
| 3.18 C₃H₇ | 2-Cl | 3.12 | |
| 3.19 CH₃ | 2,5-Cl | 3.13 | |
| 3.20 C₃H₇ | 3,5-Cl | 3.14 | |
| 3.21 CH₃ | 4-Br | 3.15 | |
| 3.22 C₂H₅ | 3-Br | 3.16 | |
| 3.23 C₃H₇ | 3-Br | 3.17 | |
| 3.24 CH₂OCH₃ | 3-Br | 3.18 | |
| 3.25 CH₃ | 2-Br | 3.19 | |
| 3.26 CH₃ | 4-CH₃ | 3.20 | |
| 3.27 CH₃ | 3-CH₃ | 3.21 | |
| 3.28 C₂H₅ | 3-CH₃ | 3.22 | |
| 3.29 C₃H₇ | 3-CH₃ | 3.23 | |
| 3.30 CH₂OCH₃ | 3-CH₃ | 3.24 | |
| 3.31 CH₃ | 2-CH₃ | 3.25 | |
| 3.32 CH₃ | 4-t.Butyl | 3.26 | |
| 3.33 CH₃ | 2,4-CH₃ | 3.27 | |
| 3.34 CH₃ | 2-Cl-4-CH₃ | 3.28 | |
| 3.35 CH₃ | 3,5-Cl | 3.29 | |
| 3.36 CH₃ | 3-CF₃ | | 186 |
| 3.37 CH₂OCH₃ | 3-CF₃ | 3.30 | |
| 3.38 C₂H₅ | 3-CH₃ | 3.31 | |
| 3.39 C₃H₇ | 3-CF₃ | 3.32 | |
| 3.40 CH₃ | 4-OCH₃ | 3.37 | |
| 3.41 CH₃ | 3-OCH₃ | 3.38 | |
| 3.42 CH₃ | 3-OC₂H₅ | 3.39 | |
| 3.43 CH₃ | 3-CN | 3.40 | |
| 3.44 C₂H₅ | 3-CN | 3.41 | |
| 3.45 C₃H₇ | 3-CN | 3.42 | |
| 3.46 CH₂OCH₃ | 3-CN | 3.43 | |

The N-(2-acetamido-5-(3-trifluoromethylphenylsulfonyloxy)-phenyl)-N',N''-bismethoxycarbonylguanidine (formula IV) with a melting point of 152° which is required for the preparation of the process product according to Example 3.36 is obtained, in a manner corresponding to Example 3 of German Offenlegungsschrift No. 2,608,238, from 2-nitro-4-(3-trifluoromethylphenoxysulfonyl)-chlorobenzene, with a melting point of 65° C., via 2-nitro-4-(3-trifluoromethylphenoxysulfonyl)-aniline, with a melting point of 130° C., 2-nitro-4-(3-trifluoromethylphenoxysulfonyl)-aniline, with a melting point of 130° C., and 2-nitro-4-(3-trifluoromethylphenoxysulfonyl)-acetanilide, with a melting point of 114° C., and 2-amino-4-(3-trifluoromethylphenoxysulfonyl)-acetanilide, with a melting point of 141° C.

EXAMPLE 6 (STILL PROCESS B))

2.5 g of N-(2-methoxyacetamido-5-phenylsulfonyloxyphenyl)-N',N''-bismethoxycarbonylguanidine (formula IV) in 25 ml of acetone and 25 ml of water are heated at 90° C. in an autoclave for 24 hours. After cooling, the crude product is filtered off. It is purified by stirring the product several times in 25 ml of 0.5 N HCl at room temperature, filtering off undissolved matter each time and adding ammonia to the filtrates. After filtering, and drying the filter residue, 0.5 g of pure N-(2-methoxyacetamido-5-phenylsulfonyloxyphenyl)-N'-methoxycarbonylguanidine, which has a melting point of 190° C. (decomposition) and which is identical with the process product obtainable in accordance with Example 1, is obtained.

EXAMPLE 7 (SALT FORMATION)

24 g of the free N-(2-methoxyacetamido-5-phenylsulfonyloxyphenyl)-N'-methoxycarbonylguanidine which can be obtained in accordance with Example 1 are stirred in 250 ml of methanol and the mixture is acidified to the colour change of Congo Red with alcoholic hydrogen chloride solution. The solution is then evaporated to dryness under reduced pressure, ether is added to the residue and the hydrochloride of N-(2-methoxyacetamido-5-phenylsulfonyloxyphenyl)-N'-methoxyacarbonylguanidine is filtered off. After washing the product with ether and drying over caustic soda under reduced pressure, the yield is 25 g. The hydrochlorides of the remaining process products, such as are described in Examples 2 to 6, are obtained in an analogous manner.

What is claimed is:

1. A monocarboxylate of phenylguanidinesulfonic acid ester of the formula

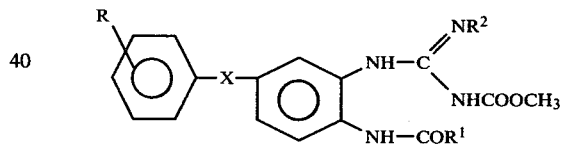

wherein X is —OSO₂— or —SO₂O—, R is hydrogen, halogen, alkyl having 1 to 4 carbon atoms, alkoxy having 1 to 4 carbon atoms, —CN or —CF₃, R¹ is hydrogen, alkyl having 1 to 5 carbon atoms, methoxymethyl, phenoxymethyl, alkoxy, alkoxyalkyl or aralkyl and R² is hydrogen, alkyl, cycloalkyl, cycloalkylalkyl or aralkyl and physiologically acceptable salts thereof with an organic or inorganic acid.

2. An anthelmintically active pharmaceutical composition containing an effective amount of a compound as defined in claim 1 in admixture with a pharmaceutically acceptable excipient or constituent.

3. A method for combating helminths and liver flukes in humans and animals infected therewith which comprises administering an effective amount of a compound as defined in claim 1.

4. The monocarbonxylate of phenylguanidinesulfonic acid ester of claim 1 wherein X is —SO₂O—, R is meta-trifluoromethyl, R¹ is methyl, ethyl, propyl, or methoxymethyl and R² is hydrogen.

* * * * *